United States Patent [19]

Malata et al.

[11] 3,967,380

[45] July 6, 1976

[54] CLAMPING MECHANISM FOR RECIPROCATING DENTAL TOOL

[75] Inventors: Peter Malata; Josef Buchsteiner, both of Burmoos; Otto Rosenstatter, Seeham, all of Austria

[73] Assignee: Dentalwerk Burmoos Gesellschaft m.b.H., Burmoos, Austria

[22] Filed: Aug. 23, 1974

[21] Appl. No.: 500,019

[52] U.S. Cl. .................................... 32/27; 32/57
[51] Int. Cl.² .............................................. A61C 1/10
[58] Field of Search ............ 279/1 TS, 27, 28, 103; 32/26, 27, 57, 58, 59

[56] References Cited
UNITED STATES PATENTS

| | | | |
|---|---|---|---|
| 649,642 | 5/1900 | Ludwig | 32/26 |
| 2,792,630 | 5/1957 | Kaltenbach | 32/27 |
| 3,171,663 | 3/1965 | Stark | 279/1 TS |

Primary Examiner—Robert Peshock
Attorney, Agent, or Firm—Toren, McGeady and Stanger

[57] ABSTRACT

In a tool holder assembly for a reciprocating dental tool including a hollow tool holder defining a tool holder chamber therein within which a dental tool may be mounted, a clamping mechanism is provided whereby a plurality of clamping balls are located about the periphery of the tool holder in order to impart a radial force to a tool body positioned within the holder. The tool holder includes a plurality of bores extending to its internal tool holder chamber and a clamping nut having a conically shaped inner surface engages the clamping balls and imparts thereto a radial force so that the balls, which are loosely mounted within the bores, may extend to within the tool holder chamber to clamp a tool therein.

9 Claims, 4 Drawing Figures

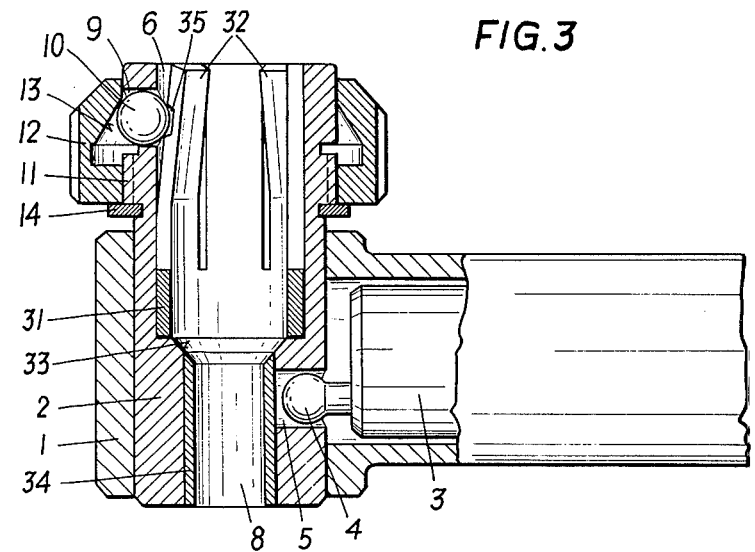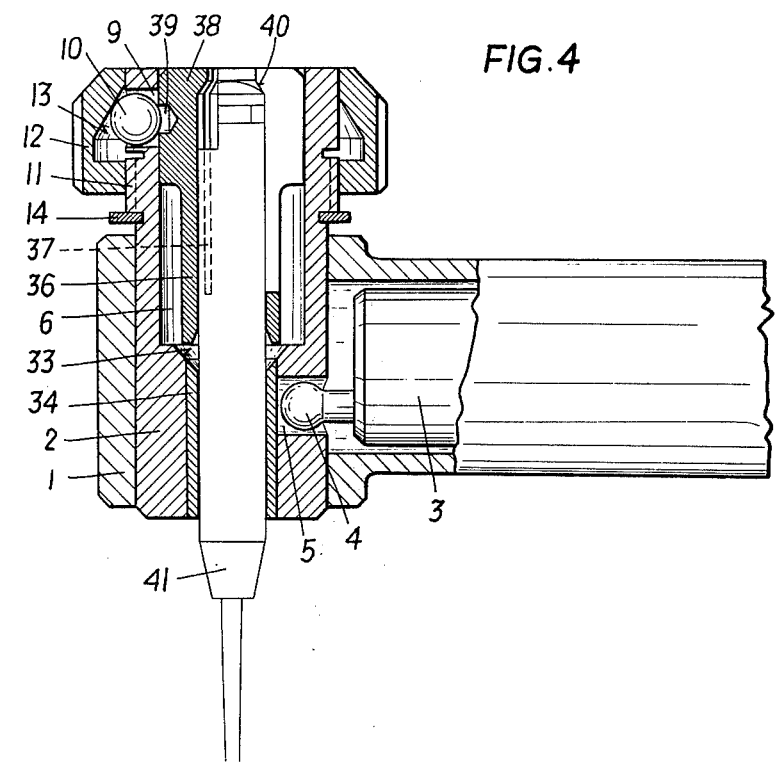

CLAMPING MECHANISM FOR RECIPROCATING DENTAL TOOL

BACKGROUND OF THE INVENTION

The present invention relates generally to dental tools and more particularly to an assembly for a holder for a reciprocating tool particularly useful for filing operations performed in the practice of dentistry. The invention further relates to such a filing tool which is held in the chamber of the tool holder which receives the tool shaft and which includes a clamping device whereby at least one clamping element is pressed laterall against the tool shaft by means of the inner conical surface of a clamping nut.

In a known tool holder assembly of this type used in the practice of dentistry, a conical clamping shaft is arranged in a correspondingly shaped chamber of the tool holder in a manner to be displaced within the tool holder by means of a screw cap. In the operations of such a device, the shaft of the tool which is introduced into the tool holder from the front thereof, is rigidly connected with the tool holder by a clamping effect. However, the disadvantage of such a known arrangement involves the fact that the clamping path of the conical clamping chuck is quite short so that only tools having a certain shaft diameter maybe clamped therein.

It has been found desirable to provide a holder assembly which is capable of having inserted therein so called handfiling tools. However, a problem arises in that handles of various filing tools having different diameters and different lengths. One approach has involved the suggestion of inserting the handles of such filing tools within a tool holder chamber and to brace the tools in a length-wise manner. By utilizing corresponding conical designs for the chamber bottom and for the clamping element, the tool handle may be centered in place. However, such a tool handle involves the disadvantage that only handles having substantially equivalent lengths and outer configurations may be clamped in the same tool holder and it therefore becomes necessary to utilize intermediate pieces in order to adapt the tool holder to a different tool length.

The present invention is intended to overcome the disadvantages of known tool holders for reciprocating dental filing tools and to provide a design whereby the tool holder is capable of clamping all types of conventional handles of hand filing tools. This is achieved by virtue of the particular clamping mechanism of the present invention which enables the application of a radial clamping force to the tool holder in order to properly hold it in place during its reciprocating operating motion.

SUMMARY OF THE INVENTION

Briefly, the present invention may be described as a reciprocating tool holder assembly, particularly suitable for mounting a filing tool useful in the practice of dentistry, such assembly comprising, in combination, a hollow generally cylindrical tool holder defining therein a tool holder chamber adapted to have inserted therein a tool, means engaging the tool holder to produce reciprocating motion thereof, a plurality of bores formed through the walls of the tool holder extending to said tool holder chamber, a plurality of clamping members loosely fitted one within each of said bores and configured to partially extend to within said tool holder chamber to effect a radial clamping force against a body located within the chamber, the bores being configured to be abutted by the clamping members to limit radial displacement of the clamping members interiorly of the chamber, a clamping nut adjustably engaged upon the tool holder and having defined thereon a conical surface located to engage the clamping members and adapted to force the clamping members radially inwardly of the chamber upon adjustable positioning relative to the tool holder, and a conically shaped internal abutment surface defined interiorly of the tool holder chamber and adapted to be engaged by a complementary surface of a body placed within the chamber for axially positioning a tool within the chamber. When a tool is inserted within the tool holder chamber it may be axially positioned by operation of the internal abutment surface. By manipulation of the clamping nut the tool may have applied thereto a radially directed clamping force which is imparted by the engagement of the clamping nut against the clamping members to force the members inwardly toward the tool holder chamber thereby to hold the tool in place during operation of the device.

The clamping members may be spherical balls loosely fitted within the bores of the tool holder.

In one aspect of the invention, a resilient sleeve may be located within the tool holder chamber with the sleeve being adapted to have a tool mounted therein. The resilient sleeve comprises a plurality of resilient clamping tongues which are engaged by the clamping members to hold the tool in place.

By a further aspect of the invention a conically shaped internal abutment surface may be defined upon a base member which is located within the tool holder chamber and which is configured to define said abutment surface as a terminal surface of the chamber. The base member may be adjustably positionable within the tool chamber and by engagement of the end of the tool against the conical abutment surface axially positioning at any appropriate location of the tool may be effected.

The various features of novelty which characterize the invention are pointed out with particularity in the claims annexed to and forming a part of this disclosure. For a better understanding of the invention, its operating advantages and specific objects attained by its use, reference should be had to the accompanying drawings and the descriptive matter in which there are illustrated and described preferred embodiments of the invention.

DESCRIPTION OF THE DRAWINGS

In the drawings:

FIG. 3 is a sectional view of a third embodiment of the invention; and

FIG. 4 is a sectional view of a fourth embodiment of the invention.

DETAILED DESCRIPTION OF THE PREFERRED EMBODIMENTS

Figure 1:
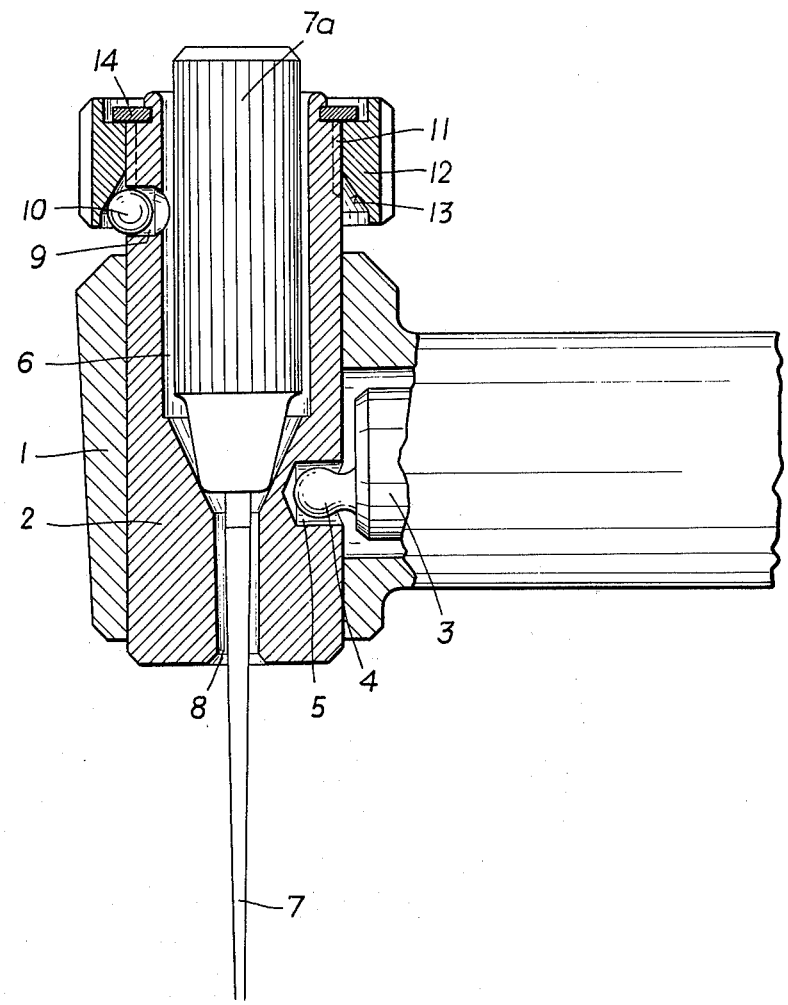
FIG. 1 is a sectional view of a first embodiment of the invention.

Referring now to the drawings, wherein like reference numerals refer to similar parts throughout the various figures thereof, a dental hand piece for mounting a reciprocating filing tool is shown as comprised of a head having slidingly mounted therein a tool holder 2. A shaft 3 having a driving pin 4 engaged within a corresponding recess 5 of the tool holder imparts by operation thereof reciprocating axial and partially rotary movement to the tool holder 2. A tool holder chamber 6 defined within the tool holder 2 is configured to have inserted therein the handle 7a of a filing tool 7 which extends through a bore 8 of the tool holder 2.

Adjacent the tool holder chamber 6 and extending through the walls thereof there is provided a plurality of bores 9 having a conical configuration with a narrower end adjacent to the chamber 6. Fitted into each of the bores 9 and loosely held therein is a clamping member 10 in the form of a spherical ball which is configured to protrude through the end of the bore 9 terminating at the inner wall of the holder 2. The inner end of bore 9 forms a constriction whereby the ball 10 may be maintained in place while partially extending into the chamber 6 to effect a clamping force against a body located therein.

The tool holder 2 is provided with a male thread 11 on the upper portion of its outer surface with a clamping nut 12 being threadedly engaged thereabout. The clamping nut 12 is formed with a conical inner surface 13 which bears against the balls 10 and which operates, when the clamping nut 12 is adjustably screwed to a proper position, to impart a radially inward force against the balls 10. An annular spring 14 affixed at the upper end of the holder 2 extends radially outwardly therefrom to engage the clamping nut 12 thereby serving as a safety device preventing upward movement of the nut 12 beyond a desired limit.

With the elements in the position shown in FIG. 1, the clamping balls 10 will have a certain degree of play in the axial direction of the bores 9 but they will be prevented from falling outwardly thereof by engagement of the clamping nut 12.

The chamber 6 of the tool holder 2, which is open at its upper end, may be provided with an end cap if desired. When the clamping nut 12 is tightened it will move axially downwardly by threaded engagement with holder 2 and thereby force the clamping balls 10 radially inwardly of the bores 9 until they bear against the handle 7a to produce a clamping force between the tool and the tool holder.

Due to the fact that the clamping force is applied in a radial direction and is produced by an annular clamping member enclosing the tool 7 and the handle 7a, the connection which is achieved will be effective independently of the length of the handle 7a.

Figure 2:
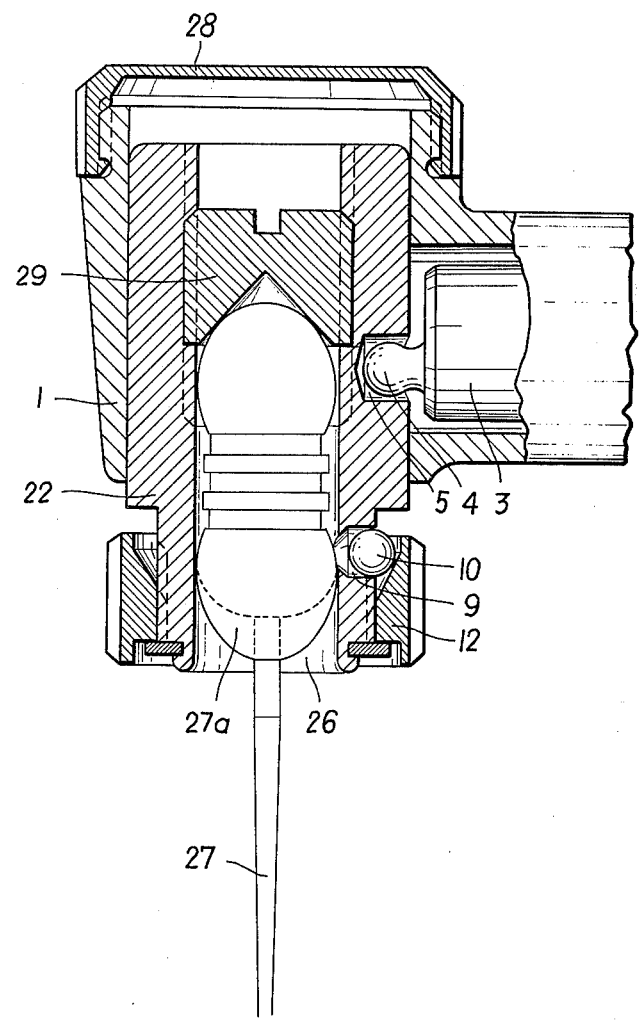
FIG. 2 is a sectional view of a second embodiment of the invention.

The present invention is of such a nature that it may be formulated in several embodiments. A second embodiment is shown in FIG. 2 as comprising a tool holder 22 having a tool holder chamber 26 which is opened at its lower end in order to enable a tool 27 with its handle 27a to be inserted through the bottom of the assembly. This creates an advantage in that tool 27 does not come into contact with a wall, such as a wall of the bore 8 shown in FIG. 1, which contact can operate to jeopardize the sterility of the tool under certain circumstances. With a chamber such as the chamber 26 of the tool holder 22 which is opened at its bottom end, it is advisable to provide a base member 29 which is adjustable in order to adapt to various dimensions the depth of the chamber. This can be accomplished, for example, by designing the base member 29 as a worm screw and as shown in FIG. 2 it will be seen that the member 29 is threadedly engaged within the inner wall of the tool holder 22.

It will be apparent that an adjustable base member can also be provided in the embodiment of FIG. 1 by structuring such a base member with the bore 8 extending therethrough.

In the embodiment according to FIG. 2, the head 1 of the hand piece has terminal screw cap 28 affixed thereto.

As in the embodiment of FIG. 1, the embodiment of FIG. 2 is provided with a similar clamping device comprising the bores 9, the balls 10 and a clamping nut 12.

A filing tool 27, similar to the tool 7, is centered in position, on the one hand by the clamping balls 10, and on the other hand by the terminal base of the chamber 6 which is defined in a conical configuration by the lower surface of the base member 29.

A third embodiment of the present invention is depicted in FIG. 3 with stops for eliminating the movement of the clamping balls 10 inwardly of the tool holder 6 being provided by a resilient sleeve 31. The resilient sleeve 31 is arranged within the chamber 6 and includes resilient clamping tongues 32 against which the clamping balls 10 may bear. The filing tool may be placed with its shaft through the bore 8 so that the handle will be received within the elastic sleeve 31. Once again the filing tool is centered by operation of the clamping balls 10 and by a conically shaped inner abutment surface 33 formed at the bottom of the chamber 6. A chuck 34 may be provided within the bore 8.

The sleeve 31 may be structured in other ways and need not be formed with the resilient clamping tongues 32. The sleeve could be constructed with a resilient configuration in many other ways, either by using a suitable resilient material or by arranging a single oblong slot in the sleeve. Additionally the sleeve 31 can be provided with a bottom or a hollow cone bottom, with or without a bore. It is possible to insert a filing tool, as shown in FIG. 1 in a turned position, so that the hand piece 1 must be turned by 180° relative to the representative position with the clamping nut 12 lying at the bottom. In this case the filing tool does not come in contact with the wall of the bore 8, and thus the parts of the tool which must be brought into contact with a tooth during dental operations cannot be contaminated. If the angle of the hand piece is used in the position shown in FIG. 3, this provides an advantage in that the tool holder 2 does not protrude with its bottom edge over the bottom side of the head 1 and there may, therefore, be no striking contact between the tool holder 2 and the tooth.

The resilient sleeve 31 is removeably mounted within the tool holder 2 so that the resilient sleeves may be exchangeably utilized. The axial positioning of the sleeve may be secured by means of recesses 35 formed on the outer side of the clamping tongues 32. Thus, for example, the sleeve 31 may be replaced by another sleeve such as the sleeve 36 which is depicted in FIG. 4.

In the embodiment shown in FIG. 4, the sleeve 36 is opened at its bottom and includes several slots 37. A sleeve head 38 fits into the chamber 6 of the tool holder and is provided with several depressions 39 which can be engaged by the clamping balls 10. Furthermore, the sleeve is provided within the range of the head 38 with a shoulder 40 which is shaped in the form of a hollow truncated cone and which forms stop means limiting the movement of a tool 42 when it is introduced into the assembly. The tool 41 shown in FIG. 4 is a conventional file having a standard shaft. The shaft can be inserted into the bore with little play, so that a satisfactory centering of the tool may be obtained.

The clamping nut 12 may be readily replaced by a loosely turning ring which has formed on its interior, taken in a circumferential direction, wedge-shaped surfaces with the number of such surfaces provided corresponding to the number of balls 10. By turning such a clamping ring, balls may be pressed radially to the inside and the wedge surfaces may be self-locking in order to secure the ring in place.

It will be seen that the present invention provides in a dental hand tool, the ability to have mounted therein practically all conventionally shaped filing tools. Such, a wide variety of differently configured filing tools can be clamped into the hand piece of the present invention despite the fact that they may differ substantially from each other in length, diameter, material, surface finish and form.

While specific embodiments of the invention have been shown and described in detail to illustrate the application of the inventive principles, it will be understood that the invention may be embodied otherwise without departing from such principles.

What is claimed is:

1. A reciprocating tool holder assembly, particularly suited for mounting a tool useful in the practice of dentistry, said assembly comprising, in combination, a hollow generally cylindrical tool holder defining therein a tool holder chamber adapted to have a tool inserted therein, means engaging said tool holder to produce reciprocating motion thereof, a plurality of bores formed through the walls of said tool holder and opening into said tool holder chamber, a plurality of generally shperically shaped clamping members, loosely fitted one within each of said bores and configured to partially extend to within said tool holder chamber to effect a radial clamping force against the body located within said chamber, said bores being shaped to limit movement of said clamping members radially inwardly of said bores to prevent said clamping members from passing through said bores into said tool holder chamber while enabling said clamping members to extend partially into said tool holder chamber to engage said tool and apply a radial clamping force thereagainst, a clamping nut adjustably engaged upon said tool holder and having defined thereon conical surface means located to engage said clamping members and adapted to force said clamping members radially inwardly of said bores toward said chamber upon adjustable positioning of said nut relative to said tool holder, and a conically shaped internal abutment surface defined interiorly of said tool holder chamber and adapted to be engaged by a complementary surface of a body placed within said chamber for axially positioning a tool within said chamber, with a tool inserted within said tool holder chamber being axially positioned by said internal abutment surface and have applied thereto a radially directed clamping force by operation of said clamping nut and said clamping members to hold said tool in place during operation of said assembly.

2. An assembly according to claim 1 wherein said clamping members are spherical balls.

3. An assembly according to claim 1 and including a resilient sleeve located within said tool holder chamber and adapted to hold therein a tool, said resilient sleeve comprising a plurality of resilient clamping tongues adapted to be engaged by said clamping members.

4. An assembly according to claim 3 wherein said resilient sleeve is removably mounted within said tool holder chamber to enable removal and replacement thereof.

5. An assembly according to claim 1 wherein said conically shaped internal abutment surface is defined by a base member located within said tool holder chamber, said base member defining said abutment surface as a terminal surface of said chamber and located to be abutted by an end of said tool for positioning said tool within said chamber, said base member being adjustably mounted relative to said tool holder to enable said tool to be positioned at different locations within said holder.

6. An assembly according to claim 5 wherein said base member comprises a worm screw threadedly engaging said tool holder.

7. An assembly according to claim 1 wherein the shape of said bores limiting movement of said clamping members radially inwardly of said bores comprises conically shaped abutment surfaces defining the side walls of said bores, said surfaces being configured to form said bores with a constricted inner opening smaller than the overall size of said clamping members, said clamping members being thereby prevented from passing through said bores and into said tool holder chamber.

8. A reciprocating tool holder assembly, particularly suited for mounting a tool useful in the practice of dentistry, said assembly comprising, in combination, a hollow generally cylindrical tool holder defining therein a tool holder chamber adapted to have a tool inserted therein, means engaging said tool holder to produce reciprocating motion thereof, a plurality of bores formed through the walls of said tool holder and opening into said tool holder chamber, a plurality of generally spherically shaped clamping members, loosely fitted one within each of said bores and configured to partially extend to within said tool holder chamber to effect a radial clamping force against the body located within said chamber, a clamping nut adjustably engaged upon said tool holder and having defined thereon conical surface means located to engage said clamping members and adapted to force said clamping members radially inwardly of said bores toward said chamber upon adjustable positioning of said nut relative to said tool holder, and a conically shaped internal abutment surface defined interiorly of said tool holder chamber and adapted to be engaged by a complementary surface of a body placed within said chamber for axially positioning a tool within said chamber, with a tool inserted within said tool holder chamber being axially positioned by said internal abutment surface and have applied thereto a radially directed clamping force by operation of said clamping nut and said clamping members to hold said tool in place during operation of said assembly.

9. An assembly according to claim 3 wherein said resilient sleeve comprises a plurality of recesses adapted to have engaged therein said clamping members.

* * * * *

UNITED STATES PATENT OFFICE
CERTIFICATE OF CORRECTION

Patent No. 3967380  Dated July 6, 1976

Inventor(s) Peter Malata et al

It is certified that error appears in the above-identified patent and that said Letters Patent are hereby corrected as shown below:

In the heading of the Patent [30] should read as follows:

--[30] FOREIGN APPLICATION PRIORITY DATA

August 28, 1973   Austria.......A 7475/73--.

Signed and Sealed this

Seventh Day of September 1976

[SEAL]

Attest:

RUTH C. MASON
*Attesting Officer*

C. MARSHALL DANN
*Commissioner of Patents and Trademarks*